(12) United States Patent
Edwards et al.

(10) Patent No.: US 8,426,175 B2
(45) Date of Patent: Apr. 23, 2013

(54) METHOD FOR THE PRODUCTION OF A FERMENTATION PRODUCT FROM A PRETREATED LIGNOCELLULOSIC FEEDSTOCK

(75) Inventors: Jason B. Edwards, Nepean (CA); Lisa McMillan, Casselman (CA); Glenn D. Munkvold, Fairchild, ME (US); Jan-Maarten Geertman, Ottawa (CA)

(73) Assignee: Iogen Energy Corporation, Ontario (CA)

( * ) Notice: Subject to any disclaimer, the term of this patent is extended or adjusted under 35 U.S.C. 154(b) by 0 days.

(21) Appl. No.: 13/466,417

(22) Filed: May 8, 2012

(65) Prior Publication Data

US 2012/0252085 A1    Oct. 4, 2012

Related U.S. Application Data

(62) Division of application No. 12/199,006, filed on Aug. 27, 2008, now Pat. No. 8,192,968.

(60) Provisional application No. 60/968,132, filed on Aug. 27, 2007.

(51) Int. Cl.
*C12P 7/14* (2006.01)
*C12P 7/08* (2006.01)

(52) U.S. Cl.
USPC .......................................... 435/162; 435/163

(58) Field of Classification Search ................... 435/162, 435/163
See application file for complete search history.

(56) References Cited

U.S. PATENT DOCUMENTS

| | | | |
|---|---|---|---|
| 5,789,210 | A | 8/1998 | Ho et al. |
| 6,475,768 | B1 | 11/2002 | Otero et al. |
| 7,078,201 | B2 | 7/2006 | Burmaster |
| 2002/0117445 | A1 | 8/2002 | Whiteman |
| 2003/0190742 | A1 | 10/2003 | Whiteman |
| 2006/0251762 | A1 | 11/2006 | Jansen et al. |
| 2007/0128706 | A1 | 6/2007 | Gorwa-Grauslund et al. |

FOREIGN PATENT DOCUMENTS

| | | |
|---|---|---|
| EP | 1 306 442 | 5/2003 |
| EP | 1 727 890 | 5/2008 |
| GB | 366 525 | 2/1932 |
| WO | 2005/093041 | 10/2005 |
| WO | 2006/015071 | 2/2006 |
| WO | 2007/097874 | 8/2007 |
| WO | 2007/149450 | 12/2007 |

OTHER PUBLICATIONS

Chang, et al, "Use of Sulfite and Hydrogen Peroxide to Control Bacterial Contamination in Ethanol Fermentation", Applied and Environmental Microbiology, vol. 63, No. 1 (1997) 1-6.
Johnson, et al., "Coming Clean: A New Method of Washing Yeast Using Chlorine Dioxide", The New Brewer, vol. 15, No. 5 (1998) 5-6.
Lushia, et al, "Antibiotic-Resistant Bacteria in Fuel Ethanol Fermentations", Ethanol Producer Magazine (2005).
Ramirez-Orozco, et al, "Debaryomyces hansenii growth in nonsterile seawater ClO2—peptone-containing medium", Canadian Journal of Microbiology, vol. 47 (2001) 676-79.
Silva, et al., "Continuous Fermentation Using Cell Recycle for Improving the Microbial Xylitol Production Rates", Poster 115 in Twentieth Symposium on Biotechnology for Fuels and Chemicals Program and Abstracts (May 3-7, 1998).

*Primary Examiner* — Herbert J Lilling
(74) *Attorney, Agent, or Firm* — Fitzpatrick, Cella, Harper & Scinto

(57) ABSTRACT

A method for obtaining a fermentation product from a sugar hydrolysate obtained from a feedstock containing hemicellulose, by (i) removing suspended fiber solids from said sugar hydrolysate to obtain a clarified sugar solution; (ii) fermenting xylose in the clarified sugar solution in a fermentation reaction with yeast to produce a fermentation broth comprising the fermentation product; (iii) separating the yeast from the fermentation broth to produce a yeast slurry; (vi) treating the yeast slurry thus obtained with an oxidant to kill microbial contaminants, thereby an oxidant-treated yeast slurry; (v) re-introducing at least a portion of the oxidant-treated yeast back to step (ii) to increase the concentration of yeast in said fermentation reaction; and (vi) recovering the fermentation product.

16 Claims, 10 Drawing Sheets

METHOD FOR THE PRODUCTION OF A FERMENTATION PRODUCT FROM A PRETREATED LIGNOCELLULOSIC FEEDSTOCK

RELATED APPLICATIONS

This application is a division of application Ser. No. 12/199,006, filed Aug. 27, 2008, which in turn claims the priority benefit of a provisional application No. 60/968,132 filed Aug. 27, 2007, both of which are incorporated by reference herein.

FIELD OF INVENTION

The present invention relates to a method for the production of a fermentation product. More specifically, the present invention relates to a method for the production of a fermentation product from a sugar hydrolysate obtained from a lignocellulosic feedstock comprising hemicellulose.

BACKGROUND OF THE INVENTION

Fuel ethanol is currently produced from feedstocks such as corn starch, sugar cane, and sugar beets. However, the production of ethanol from these feedstocks suffers from the limitation that much of the farmland which is suitable for their production is already in use as a food source for humans and animals. A further disadvantage of the use of these feedstocks is that fossil fuels are used in the conversion processes. Thus, these processes have only a limited impact on reducing greenhouse gases.

The production of ethanol from lignocellulose-containing feedstocks, such as agricultural wastes and forestry wastes, has received much attention in recent years due their low cost and wide availability. In addition, agricultural and forestry wastes are typically burned or land-filled, and thus using these lignocellulosic feedstocks for ethanol production offers an attractive alternative for disposing of them. Yet another advantage of these feedstocks is that a byproduct known as lignin, which remains after the cellulose conversion process, can be used as a fuel to power the process instead of fossil fuels. Several studies have concluded that, when the entire production and consumption cycle is taken into account, the use of ethanol produced from cellulose generates close to nil greenhouse gases.

Lignocellulosic materials have also been considered for producing other fermentation products besides ethanol. Examples of such products include lactic acid, sorbitol, acetic acid, citric acid, ascorbic acid, propanediol, butanediol, xylitol, acetone, and butanol.

The first chemical processing step for converting lignocellulosic feedstock to ethanol, or other fermentation products, involves breaking down the fibrous lignocellulosic material to liberate sugar monomers, such as glucose and xylose, from the feedstock for conversion to ethanol in a subsequent step of fermentation. The two primary processes to break down the fibrous material are acid or alkali hydrolysis, which involve the hydrolysis of the feedstock using a single step of chemical treatment, and enzymatic hydrolysis, which involves an acid or alkali pretreatment followed by hydrolysis with cellulase enzymes.

In acid or alkali hydrolysis, the lignocellulosic feedstock is contacted with a strong acid or alkali under conditions sufficient to hydrolyze both the cellulose and hemicellulose components of the feedstock to their monomeric constituents.

In the enzymatic hydrolysis process, the lignocellulosic feedstock is first subjected to a pretreatment under conditions which are similar to but milder than those in the acid or alkali hydrolysis process. The purpose of the pretreatment is to increase the cellulose surface area and convert the fibrous feedstock to a muddy texture, with limited conversion of the cellulose to glucose. If the pretreatment is conducted with acid, the hemicellulose component of the feedstock is hydrolyzed to xylose, arabinose, galactose and mannose, while alkali pretreatment does not hydrolyze sugar polymers, but rather opens up the surface of the substrate by reacting with acidic groups present on the hemicellulose. After pretreatment, the cellulose is hydrolyzed to glucose in a subsequent step that employs cellulase enzymes.

Cellulase is a generic term denoting a multi-enzyme mixture comprising exo-cellobiohydrolases (CBH), endoglucanases (EG), β-glucosidase, xylanases and β-xylosidase. The CBH and EG enzymes catalyze the hydrolysis of the cellulose β-1,4-D-glucan linkages). The CBH enzymes, CBHI and CBHII, act on the ends of the glucose polymers in cellulose microfibrils and liberate cellobiose, while the EG enzymes act at random locations on the cellulose. Together, cellulase enzymes hydrolyze cellulose to cellobiose, which, in turn, is hydrolyzed to glucose by β-glucosidase. The xylanase enzymes, such as xylanase 1 (Xyn1), xylanase 2 (Xyn2) and β-xylosidase, are typically present in the cellulase enzyme mixture and hydrolyze any xylan present in the feedstock. The presence of such enzymes may be advantageous in cases where significant amounts of xylan are present in the pretreated feedstock.

The next step of the process involves subjecting the sugar stream to fermentation to produce ethanol or other fermentation products. If glucose is the predominant substrate present, the fermentation is typically carried out with a *Saccharomyces* spp. yeast which converts this sugar and other hexose sugars present to ethanol. Furthermore, the pentose sugar, xylose, which arises from acidic pretreatment, can be fermented to ethanol, although wild-type *Saccharomyces* strains do not naturally contain the genes required for converting xylose to ethanol, and thus must be introduced into the yeast to allow for this conversion. Recombinant yeasts that are able to convert xylose to ethanol are described, for example, in U.S. Pat. No. 5,789,210, U.S. Pat. No. 6,475,768 and European Patent No. EP 1 727 890 B1.

One problem with the fermentation of sugar to ethanol, particularly the fermentation of xylose to ethanol, is that the efficiency of the process is limited by the slow kinetics of the reaction. In order to increase the volumetric rate of conversion of xylose to ethanol, it is known to increase the concentration of yeast in the fermentor. This may be carried out by continuously separating yeast from the harvested fermentation broth, such as by centrifugation, and then re-circulating the yeast back to the fermentor. The ethanol in the liquid resulting from the separation of the yeast is recovered by distillation or other known techniques. By re-introducing yeast back to the reactor in this manner, the concentration of yeast in the fermentor is continuously increased, which, in turn, substantially increases the volumetric productivity of the fermentation.

However, a problem with repeated re-circulation of yeast is that microbes, such as bacteria, are also recycled along with the yeast. This can lead to increased levels of microbial contaminants and can result in the production of unwanted fermentation products such as lactic acid. The presence of microbial contaminants producing lactic acid decreases the yield of the desired fermentation product, as well as result in a product of low purity.

A known method for disinfecting yeast-containing solutions involves washing the yeast with acid solutions, typically phosphoric or sulfuric acid, to lower the pH to below about 2.5. The goal of this treatment is to destroy contaminating microorganisms which cannot withstand low pH conditions, without a substantial reduction in yeast viability or fermentative capacity. However, washing yeast under such harshly acidic conditions subjects them to significant stress, which can reduce both viability and fermentative capacity and thus the yield of ethanol produced. Furthermore, acid washing is ineffective at destroying acid-tolerant bacteria, such as lactic acid producing bacteria.

Chang et al. (Appl. Environ. Microbiol. 63: 1-6, 1997) disclose the use of sulfite and hydrogen peroxide to control bacterial contamination in a fermentation process producing ethanol from malt extract. The sulfite treatment is performed on yeast cells removed from the fermentor and concentrated by filtration. However, bacterial contaminants (two *Lactobacillus* strains) normally found in industrial *Saccharomyces* fermentations were susceptible to sulfite only in the presence of oxygen. The addition of oxygen to the concentrated yeast slurry is not beneficial to the subsequent fermentation process, which is anaerobic. The yeast cells would therefore need to be reconditioned to anaerobic conditions in order to increase the efficiency of ethanol fermentation process. Other results presented demonstrate that hydrogen peroxide was effective in reducing the viability of one of the *Lactobacillus* species tested.

U.S. Publication Nos. 2003/0190742 and 2002/0117445 (Whiteman) disclose the sterilization of a fermentation tank between the growth of different fermentation batches by treatment with water or chlorine dioxide, followed by exposure to UV light or the addition of an acidic solution of pH 2. However, there is no disclosure of treating a yeast-containing solution to control the propagation of microbial contaminants.

British Patent No. 366,525 (Wadsworth and Wickenden) discloses the sterilization of raw sugar melt and syrups obtained from sugar cane for subsequent transportation. The sterilization involves subjecting the sugar to a weak solution of chlorine gas or liquid chlorine itself, which destroys residue of invertase, yeast and bacteria, and renders the impurities present more amenable to treatment for their subsequent removal. However, the treatment is carried out to destroy both yeast and bacteria, and thus would not be an effective method of controlling bacterial contamination in a yeast culture.

U.S. Pat. No. 7,078,201 (Burmaster) discloses a method of monitoring and controlling the oxidation-reduction potential during a fermentation of corn mash to ethanol. By raising the oxidation-reduction potential, glycerol formation is lowered, which, in turn, increases the ethanol yield. Oxidants which may be utilized for this purpose include ozone, dihalides (chlorine, bromine and iodine), chlorine dioxide, potassium permanganate and air or oxygen sparging. However, the disclosure is directed to maximizing ethanol yield by reducing glycerol production and does not address the need to control the propagation of unwanted microbes.

U.S. Publication No. 2006/0251762 (Jansen et al.) discloses that it is known to use sodium hypochlorite or chlorine dioxide to control the propagation of micro-organisms during the production of ethanol from wheat. However, the use of these oxidizing chemicals is undesirable since it can affect the "functional visco-elastic properties of the vital wheat gluten", thus reducing its quality. Furthermore, Jansen et al. teaches production of ethanol from wheat, which is a starch-containing feedstock. In starch-conversion processes, yeast recycling is not employed since conversion the fermented solutions arising from these processes contain solids and the conversion of glucose to ethanol is generally not limited by slow kinetics.

Johnson and Kunz (The New Brewer, 1998, Coming Clean—A New Method of Washing Yeast Using Chlorine Dioxide Vol. 15#5-P56) disclose the addition of chlorine dioxide to a yeast slurry during the brewing of beer. However, there is no disclosure of producing a fermentation product from a lignocellulosic feedstock comprising hemicellulose, or any mention of the specific problems encountered when converting xylose to ethanol or other fermentation products.

PCT Publication WO 2007/149450 discloses a method for preventing the growth of bacterial contaminants in yeast fermentations via the addition of stabilized chlorine dioxide to a yeast fermentation system. Although the chlorine dioxide may be added with the inoculant, or fermentable sugars prior to their addition to the fermentation system, the method is directed to the prevention of the growth of bacteria during the fermentation reaction. The method does not provide a solution for reducing bacterial contaminants that may accumulate during the yeast fermentation reaction or a solution for concentrating the yeast cells in the fermentation system to improve the efficiency of the process for fermenting hemicellulose-derived hydrolysates.

PCT Publication WO 2007/097874 also discloses a method for reducing bacterial contamination in a yeast fermentation system. In this process, chlorine dioxide is added to the fermentation system, to the fermentable carbohydrate, or to the propagation or conditioning systems used to prepare the inoculum for the fermentation. The method does not provide a solution for reducing bacterial contaminants that may accumulate during the yeast fermentation reaction or a solution for concentrating the yeast cells in the fermentation system to improve the efficiency of the process for fermenting hemicellulose-derived hydrolysates.

At present, there is much difficulty in the art to operate an efficient process for fermenting sugars obtained from the hydrolysis of hemicellulose-containing feedstocks to produce a high yield of a fermentation product. The development of an efficient process remains a critical requirement to convert such feedstocks to fermentation products, such as ethanol.

SUMMARY OF THE INVENTION

The present invention provides a method for obtaining a fermentation product from a sugar hydrolysate obtained from a feedstock comprising hemicellulose. More specifically, the present invention relates to a method for the production of a fermentation product from a feedstock comprising hemicellulose.

It is an object of the invention to provide an improved method for the production of a fermentation product from a sugar hydrolysate obtained from a pretreated lignocellulosic feedstock.

The present invention provides a method for obtaining a fermentation product from a sugar hydrolysate obtained from a feedstock comprising hemicellulose, comprising:

(i) removing suspended fiber solids from the sugar hydrolysate to obtain a clarified sugar solution;

(ii) fermenting xylose in the clarified sugar solution in a fermentation reaction with yeast to produce a fermentation broth comprising a fermentation product;

(iii) separating the yeast from the fermentation broth to produce a yeast slurry and a fermentation product, (iv) treating the yeast slurry with an oxidant to reduce microbial contaminants in the yeast slurry, thereby producing oxidant-treated yeast slurry;

(v) re-introducing at least a portion of the oxidant-treated yeast slurry back to the step of fermenting, step (ii), to increase the concentration of yeast in the fermentation reaction; and (vi) recovering the fermentation product.

The present invention provides the method as defined above, wherein in the step of treating (step iv), the oxidant is selected from the group consisting of ozone, chlorine, chlorine dioxide and potassium permanganate. Furthermore, in the step of treating (step iv), the oxidant treatment reduces concentration of the microbial contaminants in the yeast slurry to at least 100-fold lower than that of the yeast, or the concentration of microbial contaminants is reduced below about $10^3$ cfu/mL. The step of fermenting (step ii) may be conducted in a series of fermentation reactors and in the step of re-introducing (step v), the oxidant-treated yeast slurry is re-introduced back to one or more fermentation reactors in the series of fermentation reactors.

The present invention also relates to the method defined above, wherein in the step of removing (step i), the clarified sugar solution comprises a sugar selected from the group consisting of glucose, galactose, mannose, arabinose, fucose and fructose. The clarified sugar solution may also comprise an organic acid selected from the group consisting of acetic acid, glucuronic acid or galacturonic acid.

The present invention provides the method defined above, wherein in the step of fermenting (step ii), the yeast is a *Saccharomyces* spp. capable of converting xylose and glucose to ethanol. The yeast may also be a *Candida* spp. capable of converting xylose to xylitol.

The present invention is directed to the method defined above, wherein in the step of treating (step iv), the concentration of cells in the yeast slurry is between about 10 g/L and about 300 g/L.

The present invention is directed to the method defined above, wherein in the step of treating (step iv), the oxidant is added to the yeast slurry at a concentration of between about 0.5 and about 1500 ppm.

The present invention provides the method as described above, wherein in the step of treating (step iv), the yeast slurry is subjected to a temperature of between about 4° C. and about 37° C., at a pH of between about 3 and about 6, and wherein the yeast slurry is treated for a minimum of about 1 minute.

The present invention is directed to a method as defined above, wherein, the sugar hydrolysate is obtained by pretreating the lignocellulosic feedstock with a pH adjustant to produce a pretreated feedstock. The pH adjustant may be an acid. Furthermore, the step of removing suspended fibre solids may comprise washing the pretreated lignocellulosic feedstock with an aqueous solution. The clarified sugar solution may further comprise glucose resulting from a step of hydrolyzing the pretreated feedstock by enzyme hydrolysis, for example with an enzyme mixture comprising cellulase enzymes. The enzyme mixture may further comprise β-glucosidase.

The present invention also provides a method for obtaining ethanol from a feedstock comprising hemicellulose comprising:

(i) pretreating the feedstock with acid to produce a sugar hydrolysate comprising xylose;

(ii) removing suspended solids from the sugar hydrolysate to obtain a clarified sugar solution;

(iii) fermenting the clarified sugar solution in a fermentation reaction with yeast to produce a fermentation broth comprising ethanol;

(iv) separating the yeast from the fermentation broth to produce a yeast slurry;

(v) treating the yeast slurry with chlorine dioxide to kill microbial contaminants, thereby producing chlorine dioxide-treated yeast slurry;

(vi) re-introducing at least a portion of the oxidant-treated yeast slurry back to step the step of fermenting (step iii) to increase the concentration of yeast in the fermentation reaction; and (vii) recovering the ethanol.

The present invention also provides a method for obtaining xylitol from a feedstock comprising hemicellulose comprising:

(i) pretreating the feedstock with acid to produce a sugar hydrolysate comprising xylose;

(ii) removing suspended solids from the sugar hydrolysate to obtain a clarified sugar solution;

(iii) fermenting the clarified sugar solution in a fermentation reaction with yeast to produce a fermentation broth comprising xylitol;

(iv) separating the yeast from the fermentation broth to produce a yeast slurry;

(v) treating the yeast slurry with chlorine dioxide to kill microbial contaminants, thereby producing chlorine dioxide-treated yeast slurry;

(vi) re-introducing at least a portion of the oxidant-treated yeast slurry back to step the step of fermenting (step iii) to increase the concentration of yeast in the fermentation reaction; and (vii) recovering the xylitol.

The present invention overcomes difficulties in the prior art in the efficient conversion of lignocellulosic feedstock to fermentation products that involves separation and recycling of yeast to the fermentation. Recycling the yeast back to the fermentator increases the concentration of yeast during fermentation without requiring the diversion of sugars to cell growth and away from other desired fermentation products. Increasing the concentration of yeast in the fermentation increases the volumetric productivity of the fermentation, which reduces the fermentation time needed to achieve a target conversion. However, through this yeast recycle, any contaminating microorganisms that were able to grow in a previous cycle can also be recycled to the next fermentation. Contaminating microorganisms compete with yeast for available sugars, making undesirable side products, reducing yield and purity. Advantageously, it has been found that by treating the yeast slurry at this stage of the process with an oxidizing chemical, the level of contaminating microorganisms that produce unwanted byproduct, can be significantly decreased without a substantial reduction in the viability or fermentative capacity of the yeast. Therefore, by carrying out the method of the present invention, the yield of desired fermentation products, and the product purity, can be significantly improved.

BRIEF DESCRIPTION OF THE DRAWINGS

These and other features of the invention will become more apparent from the following description in which reference is made to the appended drawings wherein.

DETAILED DESCRIPTION

Figure 1:
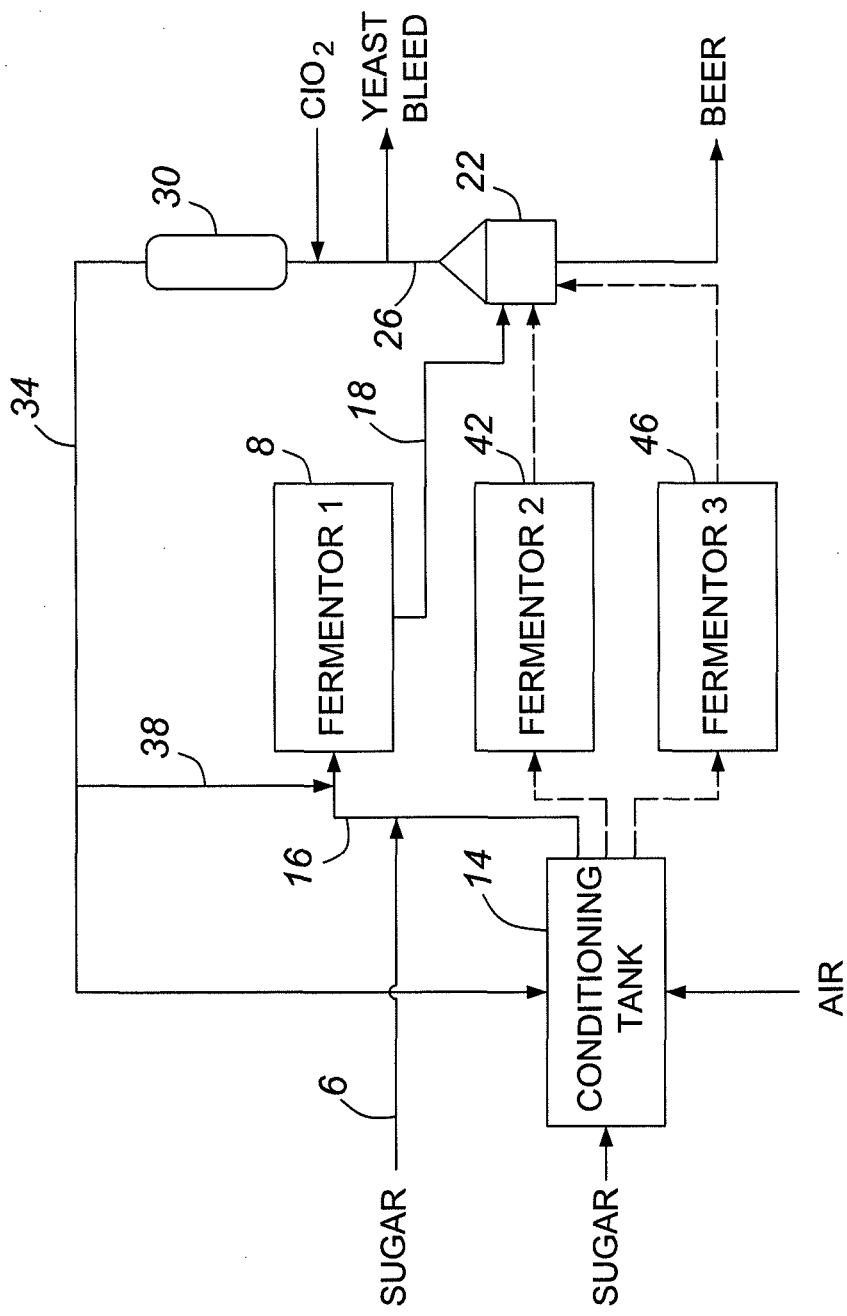
FIG. 1 shows a process flow diagram illustrating yeast recycle during fermentation with addition of chlorine dioxide after separation of the yeast according to an embodiment of the invention.

The present invention relates to a method for the production of a fermentation product from a lignocellulosic feedstock. More specifically, the present invention relates to a method for the production of a fermentation product from a feedstock comprising hemicellulose.

The following description is of an embodiment by way of example only and without limitation to the combination of features necessary for carrying the invention into effect.

The feedstock for the process of the present invention is a material comprising hemicellulose. Preferably, the feedstock is a lignocellulosic material, which includes any type of plant biomass such as, but not limited to, non-woody plant biomass, cultivated crops such as, but not limited to grasses, for example, but not limited to, C4 grasses, such as switch grass, cord grass, rye grass, miscanthus, reed canary grass, or a combination thereof, sugar processing residues, for example, but not limited to, baggase, beet pulp, or a combination thereof, agricultural residues, for example, but not limited to, soybean stover, corn stover, rice straw, rice hulls, barley straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof. Furthermore, the lignocellulosic feedstock may comprise cellulosic waste material or forestry waste materials such as, but not limited to, newsprint, cardboard and the like. Lignocellulosic feedstock may comprise one species of fiber or, alternatively, lignocellulosic feedstock may comprise a mixture of fibers that originate from different lignocellulosic feedstocks. In addition, the lignocellulosic feedstock may comprise fresh lignocellulosic feedstock, partially dried lignocellulosic feedstock, or fully dried lignocellulosic feedstock.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or any amount therebetween. The lignocellulosic feedstock also comprises lignin in an amount greater than about 10%, more typically in an amount greater than about 15% (w/w). The lignocellulosic feedstock may also comprise small amounts of sucrose, fructose and starch.

The present invention may be practiced with a feedstock material that has been pretreated. Pretreatment methods are intended to deliver a sufficient combination of mechanical and chemical action so as to disrupt the fiber structure and increase the surface area of feedstock to make it accessible to hydrolytic enzymes such as cellulases. Mechanical action typically includes the use of pressure, grinding, milling, agitation, shredding, compression/expansion and chemical action includes the use of heat (often steam), acid or alkali, and solvents.

The pretreatment is preferably a chemical treatment involving addition of a "pH adjustant". As used herein, the term "pH adjustant" is meant to encompass any acid or alkali that is suitable for disrupting fiber structure of the lignocellulosic feedstock and increasing accessibility of the lignocellulosic feedstock to being hydrolyzed in a subsequent enzymatic hydrolysis. Non-limiting examples of a pH adjustant include sulfuric acid, nitric acid, hydrochloric acid, lime and magnesium hydroxide.

Pretreatment with acid hydrolyzes the hemicellulose, or a portion thereof, that is present in the lignocellulosic feedstock to the monomeric sugars including, but not limited to, xylose, arabinose, mannose, and/or galactose, and organic acids, such as acetic acid, galacturonic acid and glucuronic acid. Preferably, the acid pretreatment is performed so that nearly complete hydrolysis of the hemicellulose and a small amount of conversion of cellulose to glucose occurs. The cellulose is hydrolyzed to glucose in a subsequent step that uses cellulase enzymes. Typically a dilute acid, at a concentration from about 0.02% (w/v) to about 2% (w/v), or any amount therebetween, (measured as the percentage weight of pure acid in the total weight of dry feedstock plus aqueous solution) is used for the pretreatment. Preferably, the acid pretreatment is carried out at a temperature of about 180° C. to about 250° C., or any temperature therebetween, for a time of about 60 seconds to about 600 seconds, or any time therebetween, at a pH of about 0.8 to about 2.0, or any pH therebetween.

One method of performing acid pretreatment of the feedstock is steam explosion, using the process conditions described in U.S. Pat. No. 4,461,648 (which is incorporated herein by reference). Another method of pretreating the feedstock slurry involves continuous pretreatment, meaning that the lignocellulosic feedstock is pumped through a reactor continuously. Continuous acid pretreatment is familiar to those skilled in the art, see, for example, U.S. Pat. No. 5,536,325, WO 2006/128304 and U.S. Pat. No. 4,237,226 (which are incorporated herein by reference). Other techniques that are known in the art and that may be used as required, include, but are not limited to, those disclosed in U.S. Pat. No. 4,556,430 (Converse et al.; which is incorporated herein by reference).

Alternatively, the pretreatment involves the addition of alkali. In contrast to acid pretreatment, pretreatment with alkali may not fully hydrolyze the hemicellulose component of the feedstock. Rather, the alkali reacts with acidic groups present on the hemicellulose. The addition of alkali may also alter the crystal structure of the cellulose so that it is more amenable to hydrolysis. Examples of alkali that may be used in the pretreatment include ammonia, ammonium hydroxide, potassium hydroxide, and sodium hydroxide. The alkali used in the pretreatment is preferably soluble in water. Examples of alkali that are insoluble in water are lime and magnesium hydroxide. When alkali pretreatment is employed, it may be advantageous to include xylanase enzyme(s) in a subsequent step of cellulase hydrolysis. Examples of suitable xylanase enzymes may include xylanase 1 and 2 (Xyn1 and Xyn2), as well as β-xylosidase.

An example of a suitable alkali pretreatment is Ammonia Freeze Explosion, or Ammonia Fiber Explosion ("AFEX" process). According to this process, the lignocellulosic feedstock is contacted with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. (See U.S. Pat. Nos. 5,171,592, 5,037,663, 4,600,590, 6,106,888, 4,356,196, 5,939,544, 6,176,176, 5,037,663 and 5,171,592, which are each incorporated herein by reference). The flashed ammonia may then be recovered according to known processes.

After acid or alkali pretreatment, the lignocellulosic feedstock may be treated to obtain a solids stream comprising the pretreated feedstock and an aqueous stream comprising soluble components. This may be carried out by washing the pretreated feedstock with an aqueous solution to produce a wash stream, and a solids stream comprising the pretreated feedstock. Alternatively, the pretreated feedstock is subjected to a solids-liquid separation, using known methods such as centrifugation, microfiltration, plate and frame filtration, crossflow filtration, pressure filtration, vacuum filtration and the like. When an acidic pretreatment is employed, the aqueous phase comprises sugars produced by the hydrolysis of hemicellulose, as well as the acid added during the pretreatment and any organic acids liberated during the pretreatment. This stream may be subsequently processed to remove the mineral acid and organic acid, and then optionally fed back to the solids stream comprising the pretreated feedstock. The aqueous stream obtained from the acid pretreated feedstock may also be subjected to the fermentation to ferment the sugars. For example, xylose present in this stream may be fermented to ethanol, xylitol, lactic acid, butanol, or a mixture thereof.

The pretreated lignocellulosic feedstock is typically slurried in an aqueous solution such as process water, fresh water, steam condensate or process recycle streams. The concentration of pretreated lignocellulosic feedstock in the slurry depends on the particle size, water retention, pump capacity and other properties of the feedstock. Typically, the concentration is between about 3% and 30% (w/w), or any amount therebetween of fiber solids (also known as suspended or undissolved solids), or between about 10% and about 20% (w/w) fibre solids, or any amount therebetween. The aqueous slurry preferably has a solids concentration that enables it to be pumped. As is well known in the art, the concentration of suspended or undissolved solids can be determined by filtering a sample of the slurry using glass microfiber filter paper, washing the filter cake with water, and drying the cake overnight at 105° C. It is preferred that the fiber solids comprise at least about 20% to about 70% cellulose by weight, or any amount therebetween. For example, the fiber solids may comprise 20%, 25%, 30%, 35%, 40%, 45%, 50%, 55%, 60%, 65% or 70% cellulose.

The pH of the pretreated feedstock is typically adjusted so that it is within a range which is optimal for the cellulase enzymes used. Generally, the pH of the pretreated feedstock is adjusted to within a range of about 3.0 to about 7.0, or any pH therebetween. For example, the pH may be within a range of about 4.0 to about 6.0, or any pH therebetween, between about 4.5 and about 5.5, or any pH therebetween, or about 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0 or any pH therebetween. If the pretreated feedstock is alkaline (i.e., if an alkali pretreatment is performed), a strong acid such as sulfuric acid may be used for the pH adjustment. If the pretreated feedstock is acidic, the pH may be adjusted with alkali selected from the group consisting of ammonia, ammonium hydroxide, lime, calcium hydroxide, potassium hydroxide, magnesium hydroxide and sodium hydroxide. For example, the alkali is selected from the group consisting of ammonia, ammonium hydroxide and sodium hydroxide.

The temperature of the pretreated feedstock is adjusted so that it is within the optimum range for the activity of the cellulase enzymes. Generally, a temperature of about 45° C. to about 55° C., or any temperature therebetween, is suitable for most cellulase enzymes, for example a temperature of 45, 46, 48, 49, 50, 51, 52, 53, 54, 55° C., or any temperature therebetween.

The cellulase enzymes and the β-glucosidase enzyme are added to the pretreated feedstock, prior to, during, or after the adjustment of the temperature and pH of the aqueous slurry after pretreatment. Preferably the cellulase enzymes and the β-glucosidase enzyme are added to the pretreated lignocellulosic feedstock after the adjustment of the temperature and pH of the slurry.

By the term "cellulase enzymes" or "cellulases," it is meant a mixture of enzymes that hydrolyze cellulose. The mixture may include glucobiohydrolases (GBH), cellobiohydrolases (CBH), endoglucanases (EG) and β-glucosidase. Although GBH enzymes may form a component of the enzyme mixture, their use in the enzymatic hydrolysis of cellulose is less common than CBH and EG enzymes. In a non-limiting example, a cellulase mixture may include CBH, EG and β-glucosidase enzymes. The GBH enzyme primarily hydrolyzes cellulose polymer chains from their ends to release glucose, while the CBH enzyme primarily hydrolyzes cellulose polymer chains from their ends to release cellobiose and the EG enzyme primarily hydrolyzes cellulose polymer in the middle of the chain. If the pretreated feedstock comprises xylan, it is especially advantageous if the enzyme hydrolysis is also carried out in the presence of one or more xylanase enzymes. Examples of xylanase enzymes that may be used for this purpose include xylanase 1, 2 (Xyn1 and Xyn2) and β-xylosidase, which are typically present in cellulase mixtures.

The process of the present invention can be carried out with any type of cellulase enzymes, regardless of their source. Non-limiting examples of cellulases which may be used in the practice of the invention include those obtained from fungi of the genera *Aspergillus, Humicola,* and *Trichoderma,* and from bacteria of the genera *Bacillus* and *Thermobifida.*

The cellulase enzyme dosage is chosen to convert the cellulose of the pretreated feedstock to glucose. For example, an appropriate cellulase dosage can be about 0.1 to about 40.0 Filter Paper Units (FPU or IU) per gram of cellulose, or any amount therebetween, for example 0.1, 0.5, 1.0, 2.0, 4.0, 6.0, 8.0, 10.0, 12.0, 14.0, 16.0, 18.0, 20.0, 22.0, 24.0, 26.0, 28.0, 30.0, 32.0, 34.0, 36.0, 38.0, 40.0 FPU (or IU) per gram of cellulose, or any amount The conversion of cellobiose to glucose is carried out by the enzyme β-glucosidase. By the term "β-glucosidase", it is meant any enzyme that hydrolyzes the glucose dimer, cellobiose, to glucose. The activity of the β-glucosidase enzyme is defined by its activity by the Enzyme Commission as EC 3.2.1.21. The β-glucosidase enzyme may come from various sources; however, in all cases, the β-glucosidase enzyme can hydrolyze cellobiose to glucose. The β-glucosidase enzyme may be a Family 1 or Family 3 glycoside hydrolase, although other family members may be used in the practice of this invention. The preferred β-glucosidase enzyme for use in this invention is the Bgl1 protein from *Trichoderma reesei*. It is also contemplated that the β-glucosidase enzyme may be modified to include a cellulose binding domain, thereby allowing this enzyme to bind to cellulose.

In practice, the hydrolysis is carried out in a hydrolysis system, which may include a series of hydrolysis reactors. The number of hydrolysis reactors in the system depends on the cost of the reactors, the volume of the aqueous slurry, and other factors. For a commercial-scale ethanol plant, the typical number of hydrolysis reactors may be 4 to 12, or any number therebetween. In order to maintain the desired hydrolysis temperature, the hydrolysis reactors may be jacketed with steam, hot water, or other heat sources. Preferably, the cellulase hydrolysis is a continuous process, with continuous feeding of pretreated lignocellulosic feedstock and withdrawal of the hydrolysate slurry. However, it should be understood that batch processes are also included within the scope of the present invention.

The enzymatic hydrolysis with cellulase enzymes produces a solution comprising glucose, unconverted cellulose and lignin. Other components that may be present in the hydrolysate slurry include the sugars xylose, arabinose, mannose and galactose, the organic acids acetic acid, glucuronic acid and galacturonic acid, as well as silica, insoluble salts and other compounds.

Although the production of a sugar hydrolysate by pretreatment, followed by cellulase hydrolysis of the pretreated feedstock, has been described, it should be understood that the aqueous sugar stream may arise from an acid or alkali treatment to affect a complete hydrolysis of the hemicellulose and cellulose components of the feedstock to their respective monomeric constituents. The hydrolysis may be carried out in two stages (see U.S. Pat. No. 5,536,325, which is incorporated herein by reference), or may be performed in a single stage.

An aqueous sugar stream comprising xylose is then fermented by one or more than one fermentation microorganism to produce a fermentation broth comprising the fermentation product. The aqueous sugar stream comprising xylose may arise at various stages in the processing of the feedstock. As described previously, an aqueous sugar stream comprising xylose and other pentose sugars arising from the pretreatment of the lignocellulosic material may be sent to fermentation. Alternatively, a stream comprising pretreated feedstock and xylose is subjected to cellulase hydrolysis. This yields a sugar hydrolysate comprising xylose and any other pentose sugars arising from pretreatment, as well as glucose resulting from the cellulase hydrolysis. In a further embodiment, a xylose-containing aqueous stream is separated from the pretreated feedstock and then is added to the stream comprising glucose obtained from the cellulase hydrolysis, thereby producing a stream comprising both glucose and xylose, along with other hexose and pentose sugars. In yet a further embodiment of the invention, the aqueous sugar stream is obtained by a complete acid or alkali hydrolysis in which both the cellulose and hemicellulose components of the feedstock are hydrolyzed to their monomeric constituents.

In a preferred embodiment, the aqueous sugar stream sent to fermentation is substantially free of undissolved solids, such as lignin and other unhydrolyzed components so that the later step of separating the yeast from the fermentation broth will result in the isolation of mainly yeast. The separation may be carried out by known techniques, including centrifugation, microfiltration, plate and frame filtration, crossflow filtration, pressure filtration, vacuum filtration and the like.

Any one of a number of known yeasts may be used to convert xylose to ethanol or other fermentation products. The yeasts may also convert other sugars, including, but not limited to glucose, present in the clarified sugar solution to a fermentation product. For example, the fermentation may be performed with recombinant *Saccharomyces* yeast engineered to ferment both hexose and pentose sugars to ethanol. Recombinant yeasts that can ferment one or both of the pentose sugars xylose and arabinose to ethanol are described in U.S. Pat. No. 5,789,210, U.S. Pat. No. 6,475,768, European Patent EP 1 727 890, European Patent EP1 863 901 and WO 2006/096130 (which are incorporated herein by reference).

When xylitol is the fermentation product, the microorganism may be a Candida yeast that is naturally capable of converting xylose to xylitol.

Preferably, the fermentation is performed at or near the temperature and pH optima of the fermentation microorganism. A typical temperature range for the fermentation of xylose to ethanol using *Saccharomyces* spp. is between about 25° C. to about 37° C. or any temperature therebetween, for example from 25, 26, 27, 28, 29, 30, 31, 32, 33, 34, 35, 36, 37° C. or any temperature therebetween, although the temperature may be higher if the yeast is naturally or genetically modified to be thermostable. For example, the temperature may be from about 25° to about 55° C., or any amount therebetween. The pH of a typical fermentation employing *Saccharomyces* spp. is between about 3 and about 6, or any pH therebetween, for example, a pH of 3.0, 3.5, 4.0, 4.5, 5.0, 5.5, 6.0, or any pH therebetween. The dose of the fermentation microorganism will depend on other factors, such as the activity of the fermentation microorganism, the desired fermentation time, the volume of the reactor and other parameters. It will be appreciated that these parameters may be adjusted as desired by one of skill in the art to achieve optimal fermentation conditions.

The sugar stream may also be supplemented with additional nutrients required for growth of the fermentation microorganism. For example, yeast extract, specific amino acids, phosphate, nitrogen sources, salts, trace elements and vitamins may be added to the hydrolysate slurry to support growth and optimize productivity of the microorganism.

The fermentation may be conducted in batch, continuous or fed-batch modes, with or without agitation. Preferably, the fermentation reactors are agitated lightly with mixing. In a typical commercial-scale fermentation, the fermentation may be conducted using a series of reactors, such as 1 to 6, or any number therebetween.

In the practice of the present invention, the fermentation is conducted so that the fermentation microorganisms are separated from the fermentation and sent back to the fermentation reaction. This may involve continuously withdrawing fermentation broth from the fermentation reactor and separating the yeast from this solution by known separation techniques to produce a yeast slurry. Examples of suitable separation techniques include, but are not limited to, centrifugation, microfiltration, plate and frame filtration, crossflow filtration, pressure filtration, settling, vacuum filtration and the like.

In the practice of the present invention, the concentration of cells (in gram dry weight per litre as measured for example in Example 2a) in the yeast slurry is from about 10 g/L to about 300 g/L. For example, the concentration of cells in the yeast slurry may be 10, 20, 30, 40, 50, 60, 70, 80, 90, 100, 110, 120, 130, 140, 150, 160, 180, 200, 220, 240, 260, 280 or 300 g/L. More preferably, the concentration of cells in the yeast slurry is from about 20 g/L to about 200 g/L.

The yeast slurry is then treated with an oxidant to destroy microbial contaminants. The oxidant may be selected from ozone, chlorine, chlorine dioxide, hydrogen peroxide and potassium permanganate. For example, the oxidant is chlorine dioxide. This oxidant destroys microbial cells via the oxidation of aromatic and sulfur-containing amino acids of the intracellular enzymes. Chlorine dioxide is particularly suitable as oxidant since bacteria are more susceptible to its effects than yeast since most bacterial enzymes are located just inside the cell membrane while most yeast enzymes reside deeper inside the cell structure.

The oxidant is preferably added to the yeast slurry at a concentration of between about 0.5 ppm and about 1500 ppm, or any concentration therebetween. For example, the oxidant may be added at a concentration of 0.5, 5, 10, 20, 30, 40, 50, 60, 70, 80, 90, 100, 200, 300, 400, 500, 600, 700, 800, 900, 1000, 1100, 1200, 1300, 1400 or 1500 ppm, or any concentration therebetween. For example, the oxidant may be chlorine dioxide and be added between about 100 and about 500 ppm, or any concentration therebetween. The chlorine dioxide may be generated using known methods, for example, by reacting chlorine gas with water and then adding sodium chlorite, or by reacting sodium hypochlorite with an acid and adding sodium chlorite.

The oxidant treatment is preferably conducted at a temperature of between about 4° C. and about 40° C., or any temperature therebetween, for example 4, 6, 8, 10, 12, 14, 16, 18, 20, 22, 24, 26, 28, 30, 32, 34, 36, 38, 40° C., or any temperature therebetween. The pH range may be between about 3 and about 6, or any pH therebetween, for example a pH of 3.0, 3.5, 4.0, 4.5, 5.0, 5.5, 6.0, or any pH therebetween. The duration of the treatment may be at least 1 minute, preferably at least 15 minutes, for example the treatment may be from 1 to about 30 min, or any time therebetween, for example 1, 2, 4, 6, 8, 10, 12, 14, 16, 18, 20, 22, 24, 26, 28, 30 minutes or any time therebetween.

The oxidant treatment preferably reduces the concentration of microbial contaminants to a level at which they no longer reduce the productivity or product yield of the xylose fermentation carried out by the yeast slurry. Preferably, the oxidant treatment reduces the concentration of microbial contaminants (in colony forming units per mL of culture or cfu/mL) to about 100-fold less than the concentration of yeast (in colony forming units per mL of culture or cfu/mL). More preferably, the oxidant treatment reduces the concentration of microbial contaminants to about $10^3$ cfu/mL or less. For example, the oxidant treatment reduces the concentration of microbial contaminants from about $10^7$ to about $10^3$ cfu/mL.

After treatment of the yeast slurry with the oxidant, the yeast is re-introduced back to the fermentation reaction. Preferably, between about 10% and about 99%, or any amount therebetween, of the yeast cells are treated and recycled. More preferably, between 80% and 95% of the yeast cells are treated and recycled. Most preferably, at least 90% of the yeast cells are treated and recycled. The practice of the invention is not limited by the number of cycles of yeast cell removal-treatment-reintroduction. Yeast recycle may be repeated at least one, or between 5 and 15 times. For example, yeast recycle may be repeated 5, 6, 7, 8, 9 10, 11, 12, 13, 14, 15 or more times.

The fermentation may employ a series of fermentation reactors. In this case, yeast is withdrawn from a reactor in the series, treated with the oxidant and then re-introduced back to one of the fermentation reactors. The oxidant-treated yeast may be fed back to the same reactor in the series or a different reactor. By re-circulating the yeast in this manner, their concentration is increased, which increases the volumetric rate of the reaction and also maximizes the yield to the desired product by minimizing the required diversion of carbon and other nutrients to yeast cell production.

Referring now to FIG. 1 there is depicted a fermentation system with recycle of yeast. FIG. 1 is included as an example of how the present invention can be practised and is not meant to be limiting in any manner. An aqueous sugar stream 6 obtained from a hemicellulose hydrolysate is fed to a first fermentation reactor 8. The sugar stream is previously treated to remove insoluble lignin and other suspended solids. The sugar stream 6 is combined with yeast from a conditioning tank 14 from line 16. The conditioning tank, in turn, is fed with a stream containing air and a portion of sugar from stream 6. A fermented solution comprising ethanol is withdrawn from the reactor 8 via line 18 and fed to a separation unit 22, typically a centrifuge, which separates the yeast from the fermented solution. Separated beer, which contains ethanol, is sent to distillation to obtain a solution enriched in ethanol. A portion of the yeast slurry in line 26 is bled. After bleeding, the balance of the yeast is washed with an aqueous solution of chlorine dioxide and then fed via line 26 to a holding tank 30 where they are held under appropriate conditions. The yeast treated with chlorine dioxide are then fed along line 34, which branches into line 38, which, in turn, introduces a portion of the yeast back to fermentor 8 to convert xylose to ethanol. The balance of the yeast is sent via line 34 to the conditioning tank 14 for cell growth. The yeast from conditioning tank 14 is then sent to second fermentor 42, and the cycle is repeated once again. This cycle may then be repeated with fermentor three 46. Although three fermentors are depicted in FIG. 1, it will be appreciated by those of skill in the art that the number of fermentors can be varied as required. Furthermore, it is contemplated that the holding tank 30 can be excluded, in which case the yeast are subsequently held, for example, in the fermentor 8 for a time sufficient to destroy microbial contaminants.

When ethanol is the product of the fermentation, it is recovered by distillation. The separated fermentation broth or beer sent to the distillation is a dilute alcohol solution which is substantially free of solids, including unconverted cellulose, although it may contain components added during the fermentation to support growth of the microorganisms, as well as small amounts of yeast that may remain after separation 16. The beer is preferably degassed to remove carbon dioxide and then pumped through one or more distillation columns to separate the alcohol from the other components in the beer. The column(s) in the distillation unit is preferably operated in a continuous mode, although it should be understood that batch processes are also encompassed by the present invention. Furthermore, the column(s) may be operated at greater than atmospheric pressure, at less than atmospheric pressure or at atmospheric pressure. Heat for the distillation process may be added at one or more points either by direct steam injection or indirectly via heat exchangers. The distillation unit may contain one or more separate beer and rectifying columns. In this case, dilute beer is sent to the beer column where it is partially concentrated. From the beer column, the vapour goes to a rectification column for further purification. Alternatively, a distillation column is employed that comprises an integral enriching or rectification section. The remaining water may be removed from the vapour by a molecular sieve resin, by adsorption, or other methods familiar to those of skill in the art. The vapour may then be condensed and denatured.

The present invention will be further illustrated in the following examples. However, it is to be understood that these examples are for illustrative purposes only, and should not be used to limit the scope of the present invention in any manner.

EXAMPLES

Example 1 describes the yeast strains used in the following examples. Example 2 describes a method for determining the efficacy of an oxidant for limiting the growth of bacterial contaminants in xylose-fermenting yeast cultures. Example 3 describes a process for producing ethanol from xylose using chlorine dioxide-treated, recycled *Saccharomyces*. Example 4 describes a process for producing xylitol from xylose using chlorine dioxide-treated, recycled *Candida*.

Example 1

Yeast Strains

The *Saccharomyces* strain used in this study is a recombinant strain containing multiple copies of the *Pichia stipitis* genes encoding xylose reductase and xylitol dehydrogenase and the *S. cerevisiae* gene encoding xylulokinase integrated into its genome as described in U.S. Pat. No. 5,789,210. The *Candida tropicalis* strain is ATCC 1369.

Example 2

14 L Fed-batch Fermentations of Recombinant *Saccharomyces* and *Candida tropicalis* with Xylose-Containing Lignocellulose Hydrolysate 2a. *Saccharomyces*

*Saccharomyces* cells from a frozen glycerol stock were used to inoculate 4 L of Sc Inoculation Medium (pH 6). The inoculum was grown with shaking at 160 rpm for 24 h at 30° C. The cells were harvested by centrifugation (4000 rpm for 5 min) and the entire cell pellet was resuspended in about 50 mL of the supernatant and this was used to inoculate 20 L of Sc Propagation Medium (pH 5.0). A fed-batch fermentation was run for 4 days with mild aeration of 56 slpm and 500 rpm agitation by mechanical stirring. The pH was maintained at 5.0 and the temperature was maintained at 30° C. for the first two days followed by 28° C. for the last two days. A 60 g/L glucose solution was fed to the vessel at a rate of 83.3 mL/h. The culture was sampled three times daily and the samples analyzed for cell growth, xylose and glucose. At the end of the fermentation, the entire broth was harvested and the cells concentrated by centrifugation (4000 rpm for 5 min in multiple 4 L Nalgene bottles). The cell pellets were resuspended to a concentration of 22.5 g cell mass/L. This was used to inoculate 10 L of Sc Fermentation Medium. Batch fermentation was run for 2-3 days with 1 slpm aeration, 250 rpm mechanical agitation. The pH was maintained at 6.0 and the temperature maintained at 28-30° C. The culture was sampled three times daily and the samples analyzed for cell growth, xylose glucose and ethanol.

| Component | Sc Inoculation Medium (g/L or mL/L) | Sc Propagation Medium (g/L or mL/L) | Sc Fermentation Medium (g/L or mL/L |
|---|---|---|---|
| Glucose | 60 | 375 | 0 |
| Lignocellulose hydrolysate solution[d] | 0 | 500 | 900 |
| 10x Mineral Media solution[a] | 100 | 100 | 100 |
| Trace elements solution[b] | 1 | 1 | 1 |
| Vitamin solution[c] | 1 | 1 | 1 |
| 1M MES buffer, | 100 | 0 | 0 |
| Yeast extract | 10 | 0 | 0 |
| peptone | 20 | 0 | 0 |
| Antifoam solution | 5 | 5-10 | 5-10 |

[a]10x Mineral media contains 50 g/L ammonium sulfate, 30 g/L potassium phosphate monobasic, 5 g/L magnesium sulfate.
[b]Trace elements solution contains 0.403M EDTA, 15.6 mM zinc sulfate, 5 mM manganese chloride, 1.3 mM cobalt chloride, 1.2 mM copper sulfate, 1.6 mM disodium molybdate, 30.6 mM calcium chloride, 10.8 mM ferrous sulfate, 16.2 mM boric acid, 0.6 mM potassium iodide
[c]Vitamin solution contains 50 mg/L biotin, 1.0 g/L calcium pantothenate, 1 g/L nicotinic acid, 1.0 g/L myoinositol, 1.0 g/L thiamine chloride hydrochloride, 1.0 g/L pyridoxal hydrochloride,
[d]Lignocellulose hydrolysate solution was prepared by the dilute acid pretreatment of wheat straw according to the methods of WO 2006/128304, and comprised 110 g/L xylose, 15 g/L glucose, 11 g/L arabinose and 5 g/L galactose in addition to other dissolved and undissolved solids.

Cell mass dry cell weight measurements were conducted as follow: 5 mL of sample was filtered through a pre-weighed Fisher Brand G6, 5.5 cm glass fiber filter The filter and its contents were dried via microwave set at 450 Watts for 16 minutes at 40% power using a Procter Silex Model #35038. The dried filter with dried cell mass was then reweighed and the mass of the filter paper subtracted.

Xylose and glucose concentrations of each sample were measured as follows: 2 mL of the broth were centrifuged at 14,000 rpm for 3 min to remove cells and the supernatant filtered through a 0.2 μm syringe filter. 10× dilutions of the supernatant were prepared in 5 mM sulfuric acid solution. Dilutions were analyzed via HPLC using an Agilent 1100 Series HPLC stem equipped with an 1100 Series Autosampler and Pumping System and Chemstation control software. A Varian MetaCarb 87H column maintained at 50° C. was used for separation. The eluant was a 5 mM aqueous sulfuric acid solution with a flow rate of 0.600 mL/min. Glucose, ethanol, xylose and xylitol were quantified using an Agilent 1100 Series Refractive Index Detector. Acetic acid and lactic acid were measured using an Agilent 1200 Series Variable Wavelength Detector.

2b. *Candida tropicalis*

*C. tropicalis* cells from a frozen glycerol stock used to inoculate 2 L of Ct Inoculation Medium. The inoculum was grown with shaking at 160 rpm for 24 h at 30° C. The cells were harvested by centrifugation and the entire cell pellet was used to inoculate 2 L of Ct Xylose Medium. This culture was grown with shaking at 160 rpm for 24 h at 30° C. and the broth was used to inoculate 10 L of Ct Fermentation Medium. Batch fermentation was run with mild aeration of 4 slpm and 150 rpm agitation by mechanical stirring. The culture was sampled three times daily and the samples analyzed for cell growth, xylose and xylitol as described in Example 2a.

| Component | Ct Inoculation Medium (g/L or mL/L) | Ct Xylose medium (g/L or mL/L) | Ct Fermentation Medium (g/L or mL/L) |
| --- | --- | --- | --- |
| Glucose | 60 | 0 | 0 |
| Lignocellulose hydrolyaste solution[d] | 0 | 800 | 800 |
| 10x Mineral Media solution[a] | 100 | 100 | 100 |
| Trace elements solution[b] | 1 | 1 | 1 |
| Vitamin solution[c] | 1 | 1 | 1 |
| 1M MES buffer, pH 5.0 | 100 | 100 | |
| Antifoam solution | 5 | 5 | 5-10 |

[a]10x Mineral media contains 50 g/L ammonium sulfate, 30 g/L potassium phosphate monobasic, 5 g/L magnesium sulfate.
[b]Trace elements solution contains 0.403M EDTA, 15.6 mM zinc sulfate, 5 mM manganese chloride, 1.3 mM cobalt chloride, 1.2 mM copper sulfate, 1.6 mM disodium molybdate, 30.6 mM calcium chloride, 10.8 mM ferrous sulfate, 16.2 mM boric acid, 0.6 mM potassium iodide
[c]Vitamin solution contains 50 mg/L biotin, 1.0 g/L calcium pantothenate, 1 g/L nicotinic acid, 1.0 g/L myoinositol, 1.0 g/L thiamine chloride hydrochloride, 1.0 g/L pyridoxal hydrochloride,
[d]Lignocellulose hydrolysate solution was prepared by the dilute acid pretreatment of wheat straw according to the methods of WO 2006/128304, and comprised 110 g/L xylose, 15 g/L glucose, 11 g/L arabinose and 5 g/L galactose in addition to other dissolved and undissolved solids.

Example 3

Control of Bacterial Contamination on a Contaminated Broth Sample

A bacterially contaminated broth sample was obtained from the pilot fermentation described in Example 2a.

Figure 2A:
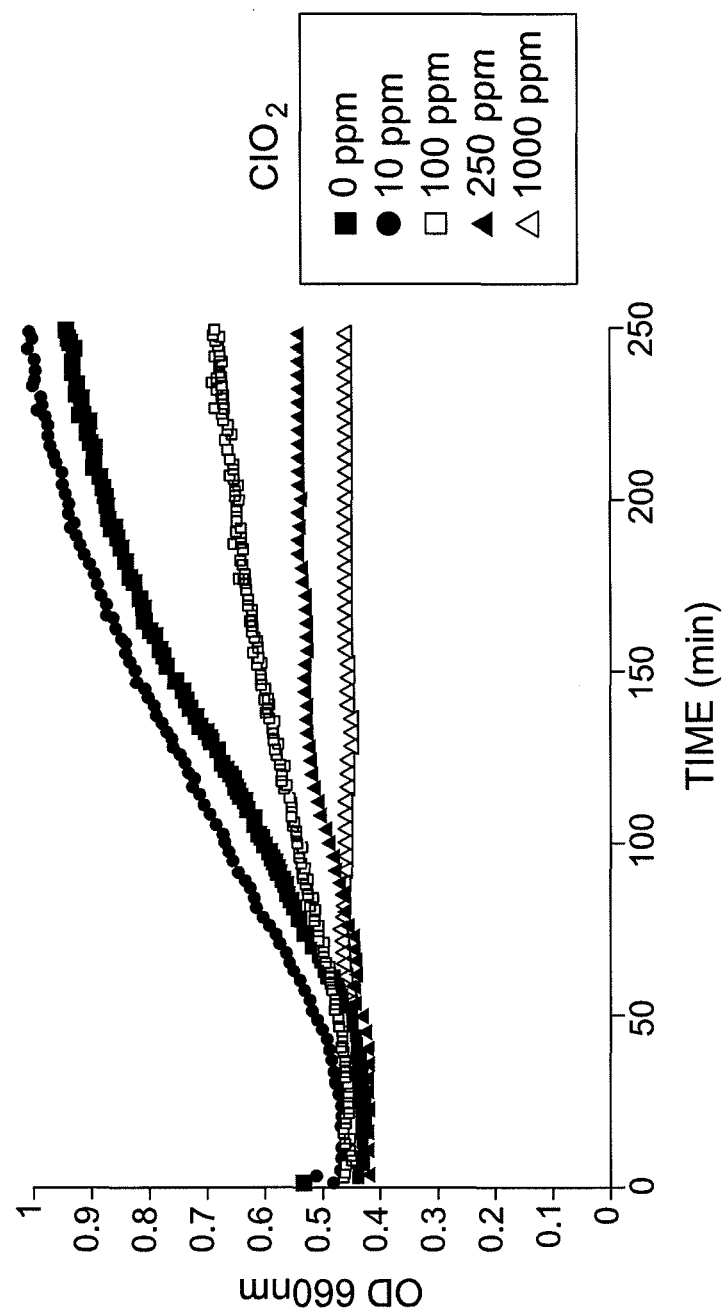
FIG. 2A shows the growth of bacterial contaminants isolated from a contaminated *Saccharomyces* pilot fermentation grown on xylose-containing lignocellulose hydrolysate in the presence of 0, 10, 100, 250 and 1000 ppm chlorine dioxide.
Figure 2B:
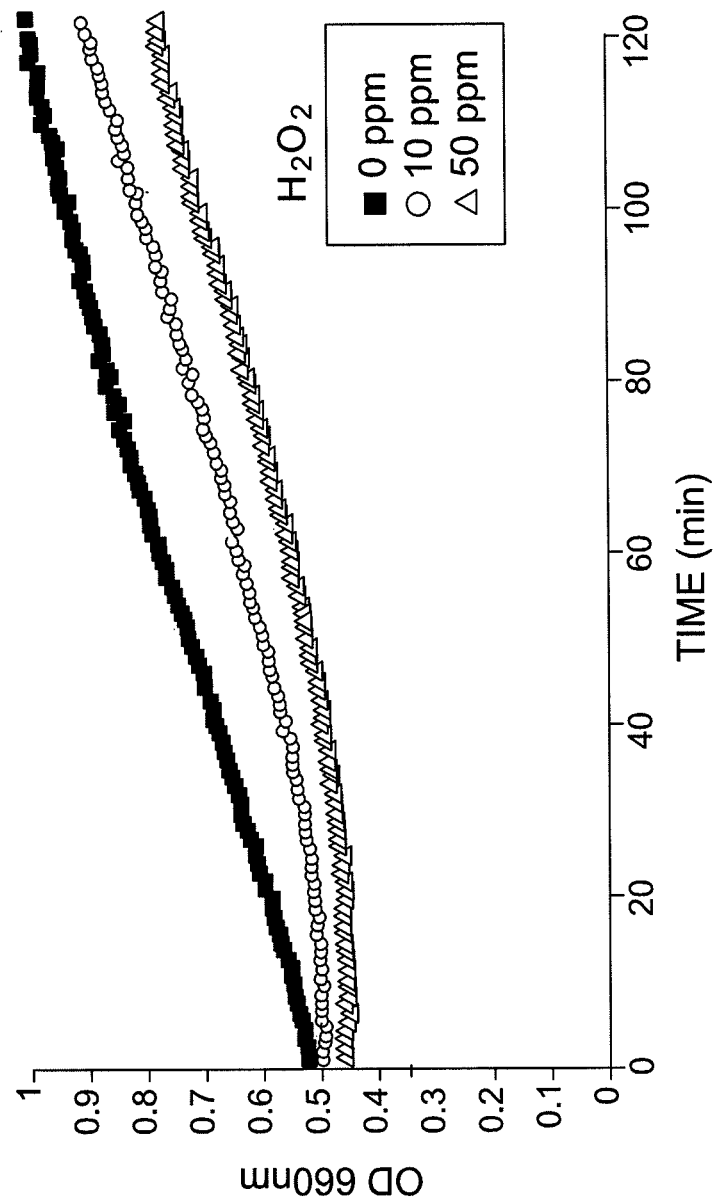
FIG. 2B shows the growth of bacterial contaminants isolated from a contaminated *Saccharomyces* pilot fermentation grown on xylose-containing lignocellulose hydrolysate in the presence of 0, 10 and 50 ppm hydrogen peroxide.
Figure 2C:
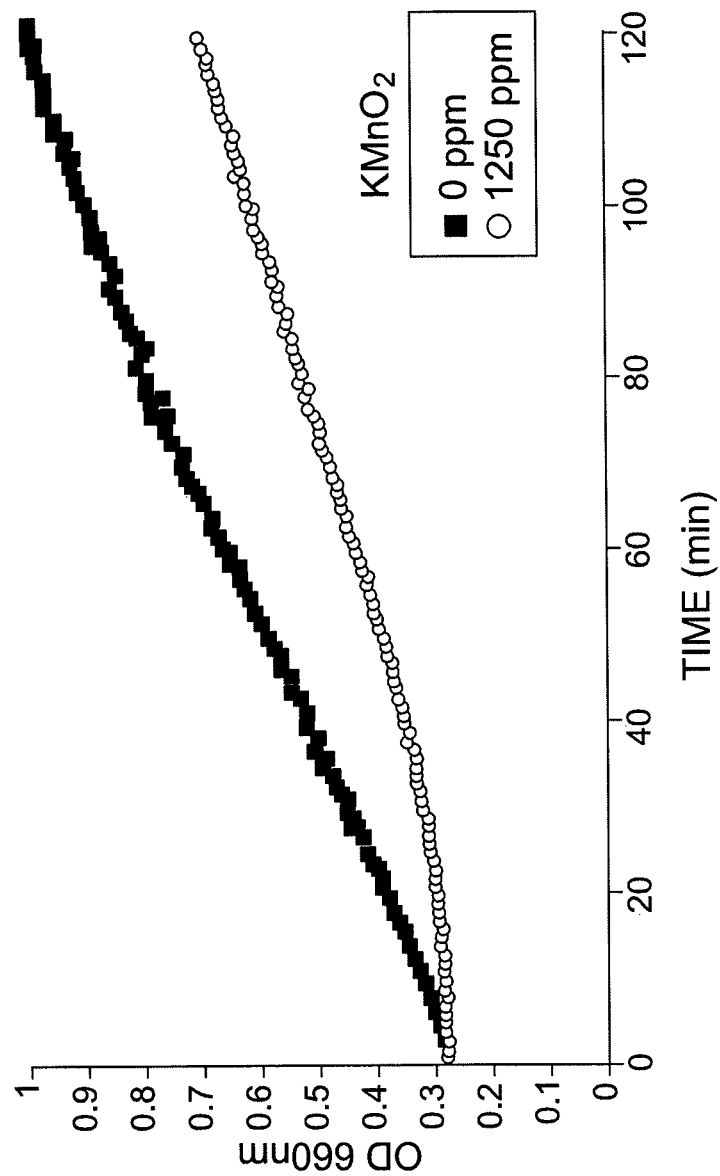
FIG. 2C shows the growth of bacterial contaminants isolated from a contaminated *Saccharomyces* pilot fermentation grown on xylose-containing lignocellulose hydrolysate in the presence of 0 and 1250 ppm potassium permanganate.

In order to isolate and selectively propagate the contaminants, samples of contaminated broth (5 mL) was filtered through a GF/A 40 mm filter paper with pore size 1.6 μm, into a 300 mL vacuum flask using vacuum filtration to remove suspended solids and yeast. It was rinsed with YEP-glucose medium (10.0 g/L yeast extract, 20.0 g/L peptone and 50.0 g/L glucose) at approximately every 1.5 mL and then rinsed with the remaining media. A total of 200 mL of media was used for rinsing. The filtrate was then transferred to an empty 300 mL flask, which was then cultivated with shaking at 160 RPM and 30° C. for approximately 16 hours. This formed the bacteria inoculum for the experiment Samples were prepared in cuvettes containing 3 mL of YEP-glucose media and 48 μL of the bacteria inoculum. Each cuvette was dosed with approximately 0, 10, 50, 100, 250, 1000, or 1250 ppm of chlorine dioxide, hydrogen peroxide or potassium permanganate as indicated in FIGS. 2A, 2B and 2C, respectively. A blank cuvette was prepared without bacteria. The cuvettes were stirred continuously and were held at 30° C. in a Cary 300 Series Spectrophotometer (Varian). The samples were then analyzed for optical density (OD660) on the Cary spectrophotometer at 660 nm over several hours.

These results are shown in FIG. 2. The figure shows that chlorine dioxide of 100 ppm or higher (FIG. 2A), hydrogen peroxide dosages of 50 ppm or higher (FIG. 2B), and potassium permanganate dosage of 1250 ppm (FIG. 2C) suppress bacterial growth (reduced rate of increase in OD660 vs the 0 ppm controls).

In a separate experiment, the entire contents of the bacteria contaminated broth from Example 2a was harvested. The yeast was concentrated by centrifugation (4 min, 4000 rpm) and resuspended in the original, contaminated supernatant to 20 g/L, 200 g/L or 300 g/L. Contamination was verified microscopically. The three slurries produced were cooled in an ice-water bath treated with either $ClO_2$ at 0, 10, 50, 250, 500, 750 and 1000 ppm, serially diluted and plated on YM agar (3.0 g/L yeast extract, 3.0 g/L malt extract, 5 g/L peptone, 10 g/L glucose, 20 g/L agar)+chloramphenicol (34 μg/mL) plates for yeast and TSA (15 g/L pancreatic casein digest, 5 g/L enzymatic soy meal digest, 5 g/L NaCl, 15 g/L agar)+cycloheximide (0.05 μg/mL) plates for bacterial enumeration. Plates were incubated overnight at 30° C. and 37° C. for yeast and bacteria, respectively. Plates were counted the next day and bacterial colonies were verified microscopically.

The results show that chlorine dioxide dosages of 250 ppm or higher effectively suppresses bacterial growth in a 20 g/L yeast cell suspension with little to no impact on yeast viability. Effective bacterial decontamination of the 200 g/L and 300 g/L yeast suspensions required chlorine dioxide dosages of 500 ppm or higher; this dosage had little or no impact on the viability of the yeast.

Example 4

Production of Ethanol from Xylose with Chlorine Dioxide-Treated, Recycled *Saccharomyces*

*Saccharomyces* cells from contaminated fermentation broth were harvested and concentrated using a lab centrifuge to produce a yeast slurry having a cell concentration of 200 g/L suspended in lignocellulose hydrolysate. The yeast slurry was treated with chlorine dioxide at 50 ppm, 300 ppm and 500 ppm. The yeast slurry was used to re-inoculate fermentors containing 10 L of Sc Fermentation Medium run in batch mode at a starting yeast concentration targeted at 22.5 g/L yeast, as described in Example 2a. The culture was sampled three times daily and the samples analyzed for xylose, lactic acid and ethanol as described in Example 2a.

Figure 3A:
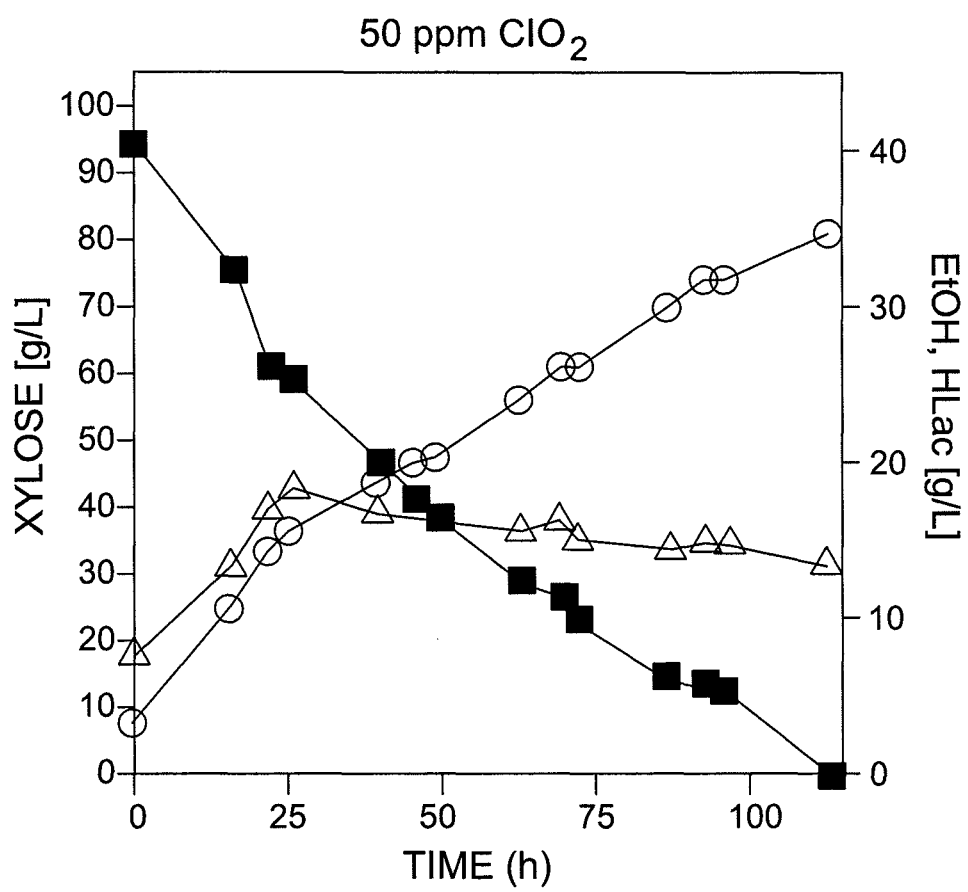
FIG. 3A shows the consumption of xylose (closed squares) and the production of ethanol (open triangles) and lactic acid (open circles) by cultures of recombinant *Saccharomyces* inoculated with a yeast slurry treated with 50 ppm $ClO_2$.
Figure 3B:
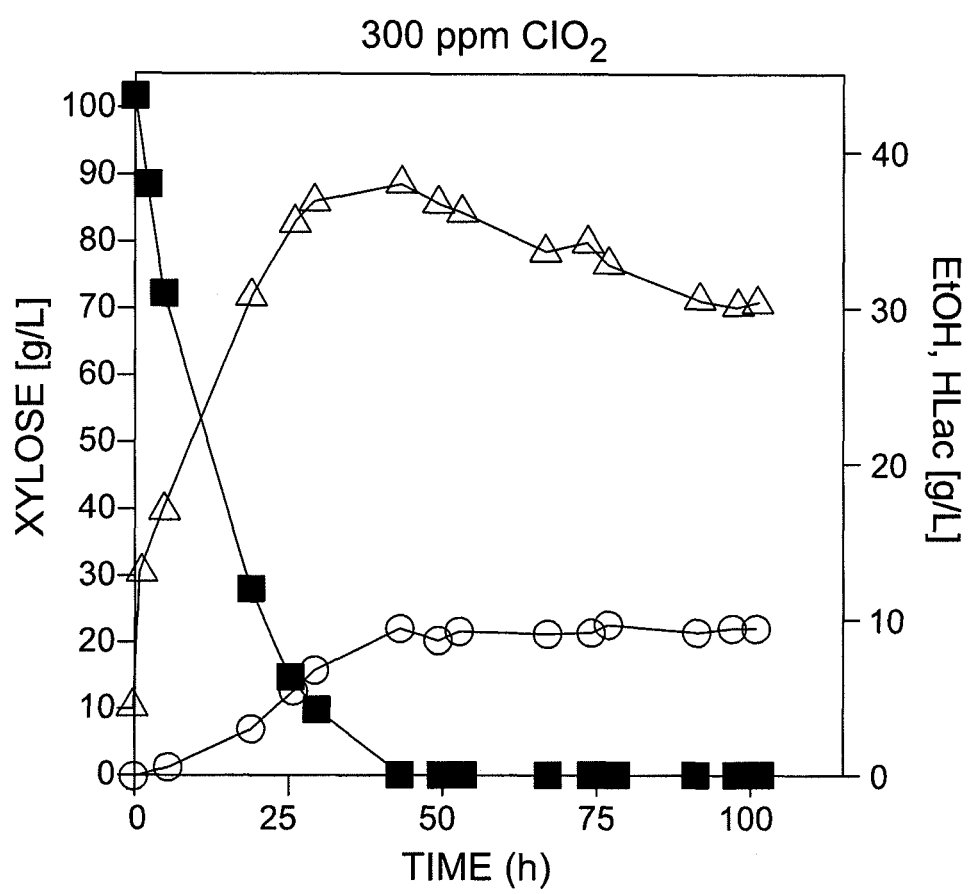
FIG. 3B shows the consumption of xylose (closed squares) and the production of ethanol (open triangles) and lactic acid (open circles) by cultures of recombinant *Saccharomyces* inoculated with a yeast slurry treated with 300 ppm $ClO_2$.
Figure 3C:
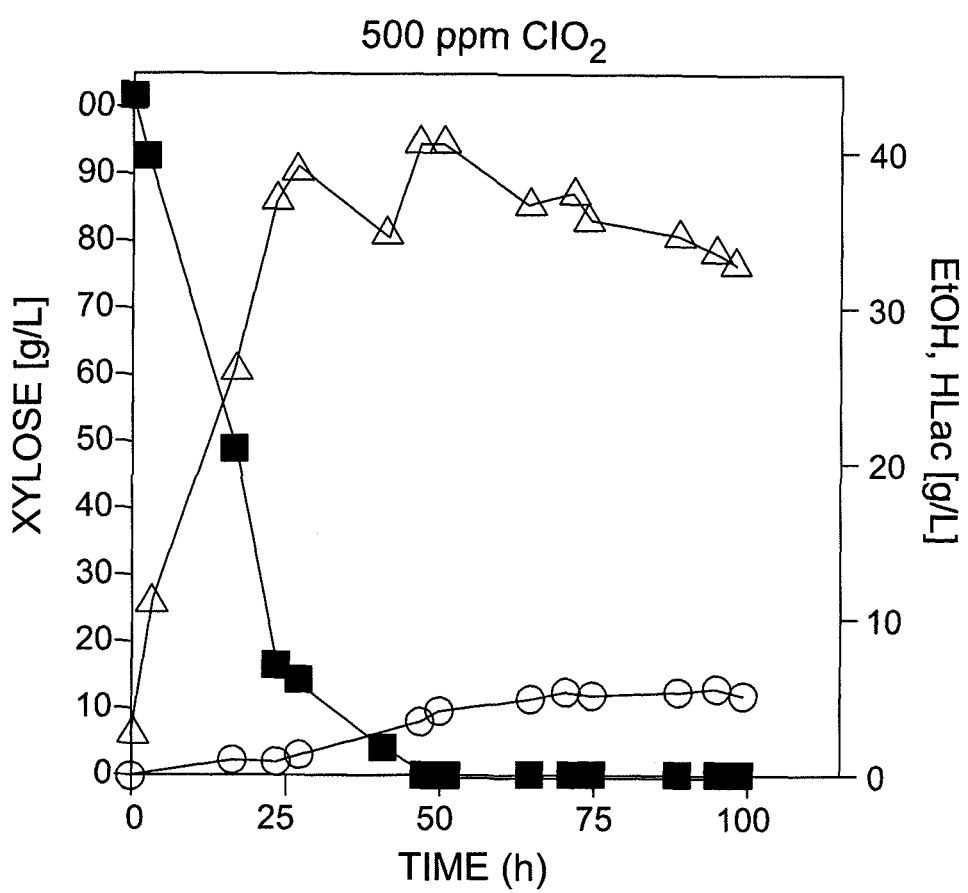
FIG. 3C shows the consumption of xylose (closed squares) and the production of ethanol (open triangles) and lactic acid (open circles) by cultures of recombinant *Saccharomyces* inoculated with a yeast slurry treated with 500 ppm $ClO_2$.
Figure 4A:
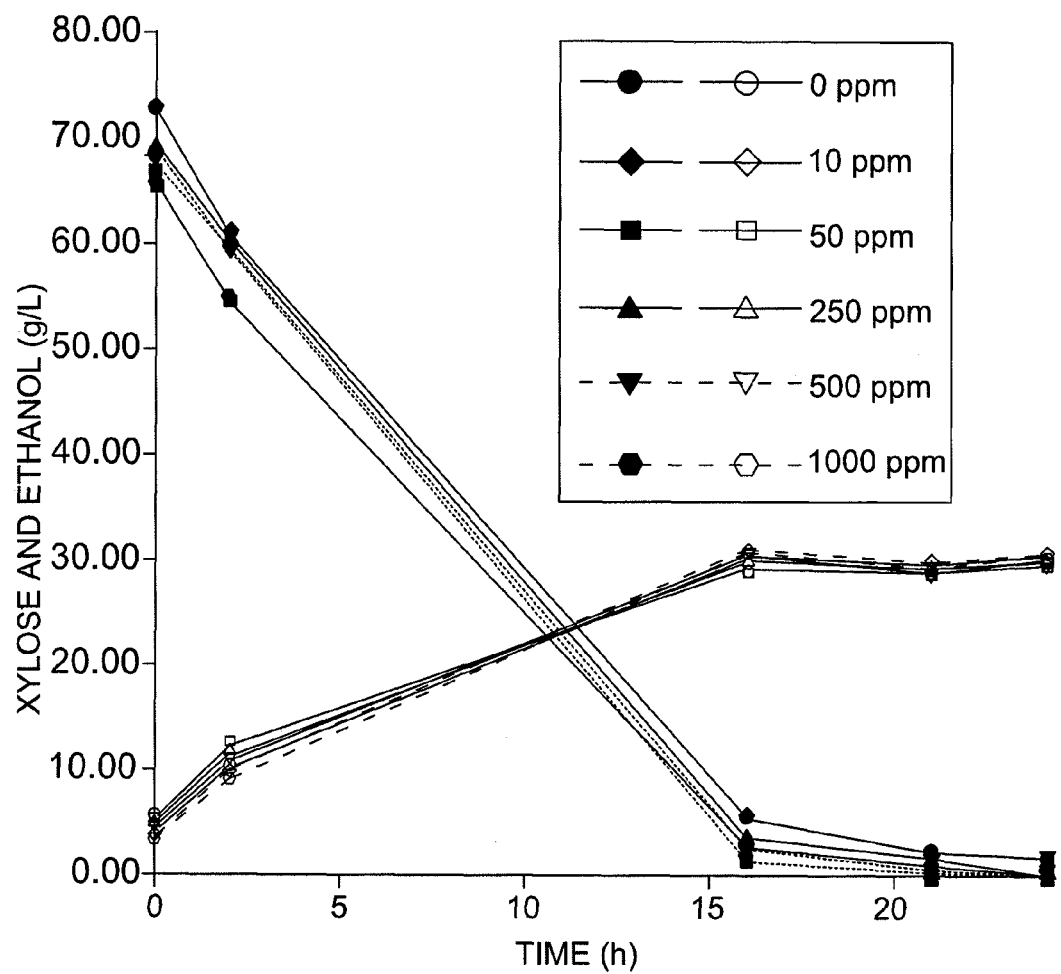
FIG. 4A shows the consumption of xylose (filled symbols) and the production of ethanol (open symbols) by recombinant *Saccharomyces* cultures inoculated with yeast slurry treated with 0, 10, 50, 250, 500 and 1000 ppm chlorine dioxide and grown on xylose-containing lignocellulose hydrolysate.
Figure 4B:
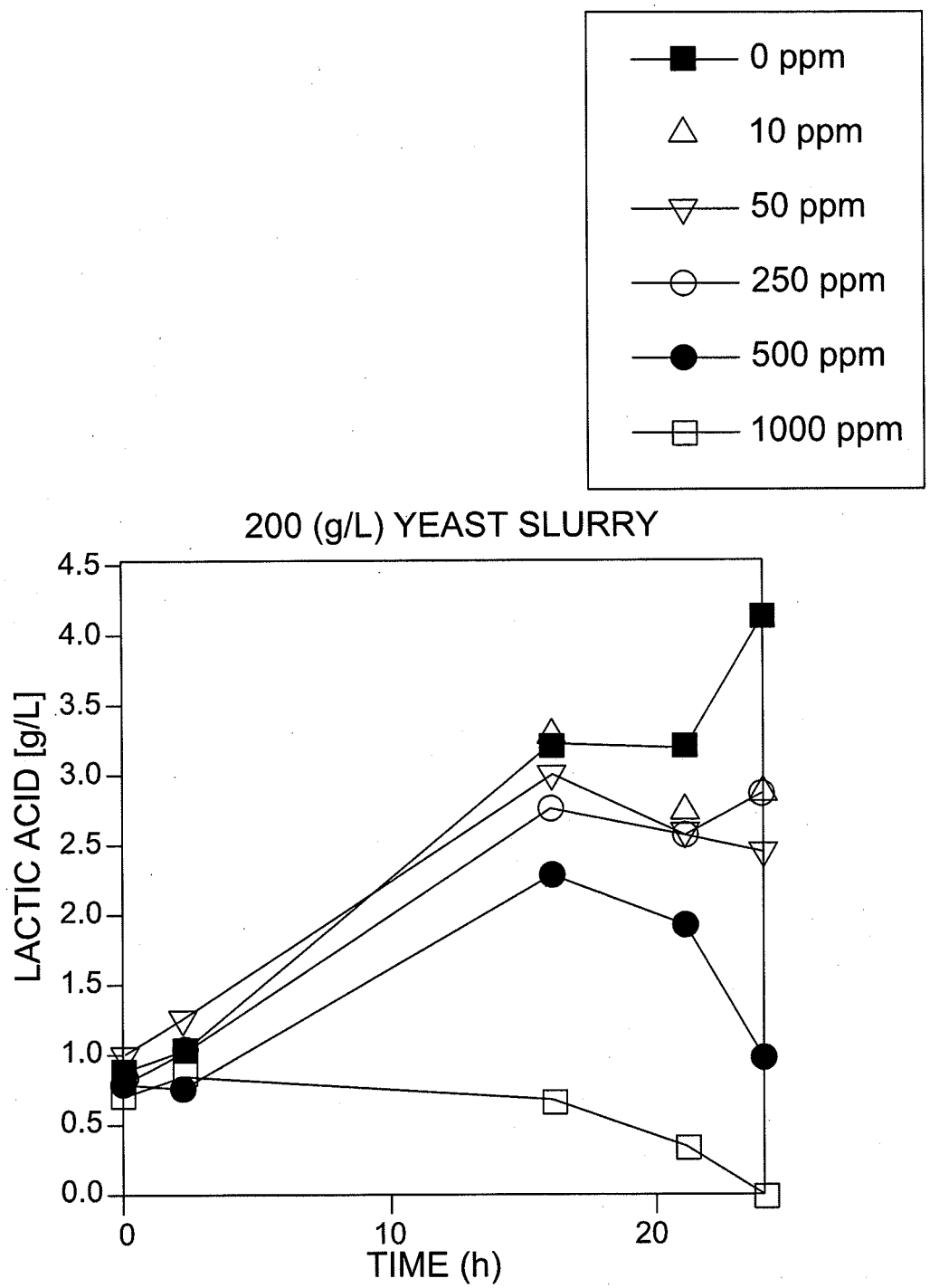
FIG. 4B shows the production of the undesired fermentation byproduct lactic acid by recombinant *Saccharomyces* cultures inoculated with yeast slurry treated with 0, 10, 50, 250, 500 and 1000 ppm chlorine dioxide and grown on xylose-containing lignocellulose hydrolysate.

The results in FIG. 3 show that cultures inoculated with a 200 g/L yeast slurry that had been treated with chlorine dioxide at 300 ppm (FIG. 3B) or 500 ppm with 300 g/L yeast slurry (FIG. 3C) produced significantly more of the desired ethanol product and less of the unwanted lactic acid byproduct than the culture inoculated from the 20 g/L yeast slurry treated with 50 ppm chlorine dioxide (FIG. 3A). In addition, the cells treated with the higher chlorine dioxide dosages showed a significantly faster rate of xylose consumption.

Example 5

Production of Xylitol from Xylose with Chlorine Dioxide-Treated, Recycled *Candida tropicalis*

Cells were harvested from the entire broth of the pilot fermentation described in Example 2b, concentrated by centrifugation and resuspended in 800 mL of supernatant and divided into two 400 mL yeast slurries. The yeast slurries were treated at room temperature with either 0 or 100 ppm of chlorine dioxide and inoculated into 10 L of Ct Fermentation medium and the batch fermentations of Example 2b were repeated with the treated and untreated yeast slurries. Samples were collected at 0 h, 21 h, 30 h, 36 h, 48 h, 60 h, 72 h, 78 h, 84 h, 96 h, 102 h, 108 h and 120 h and analyzed for xylose and xylitol as described in Example 2a.

Figure 5:
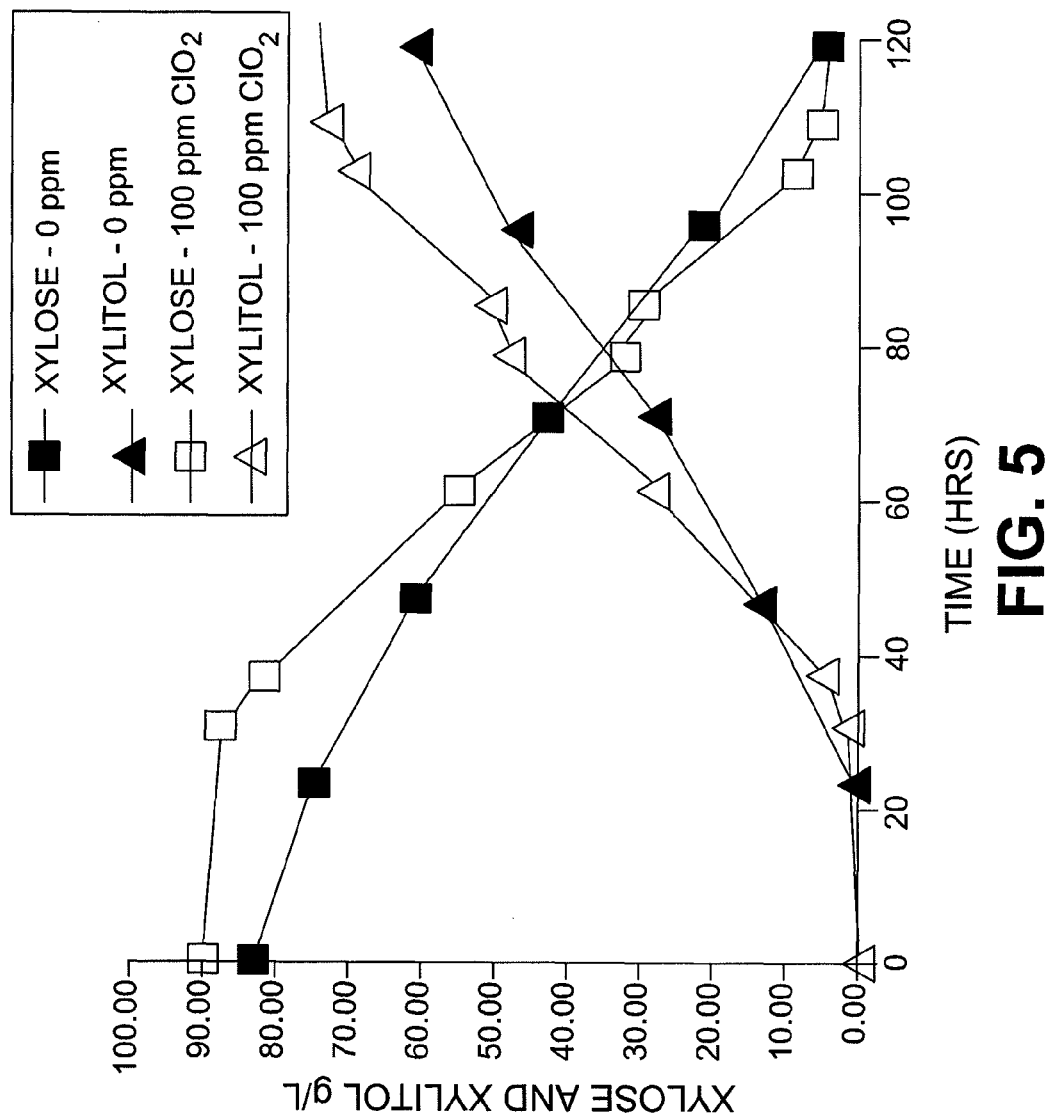
FIG. 5 shows the xylose consumption and production of a xylitol fermentation product by a bacterially contaminated *Candida tropicalis* culture inoculated with yeast slurry treated with either 0 ppm or 100 ppm chlorine dioxide.

The results in FIG. 5 show that the *C. tropicalis* culture inoculated with the treated slurry produced more of the xylitol fermentation product than the *C. tropicalis* culture inoculated with the untreated slurry.

The present invention has been described with regard to one or more embodiments. However, it will be apparent to persons skilled in the art that a number of variations and modifications can be made without departing from the scope of the invention as defined in the claims.

What is claimed is:

1. A method for obtaining ethanol from a feedstock comprising hemicellulose, comprising:
   (i) pretreating the feedstock to produce a stream comprising pretreated feedstock;
   (ii) optionally removing xylose from the stream produced in step (i);
   (iii) hydrolyzing the pretreated feedstock with an enzyme mixture comprising cellulase enzymes and beta-glucosidase to produce a sugar hydrolyzate comprising at least glucose;
   (iv) fermenting the sugar hydrolyzate in a fermentation reaction with yeast to produce a fermentation broth comprising ethanol;
   (v) withdrawing a slurry comprising yeast during the fermenting step (step iv);
   (vi) treating the slurry comprising yeast with an oxidant to kill microbial contaminants, thereby producing an oxidant-treated slurry comprising yeast;
   (vii) re-introducing at least a portion of the oxidant-treated slurry comprising yeast back to the fermenting step (step iv) to increase the concentration of yeast in the fermentation reaction; and
   (viii) recovering the ethanol.

2. The method according to claim 1, wherein in the fermenting step (step iv), the fermentation reaction is conducted in a series of fermentation reactors and wherein in the re-introducing step (step vii), the oxidant-treated slurry comprising yeast is re-introduced back to one or more fermentation reactors in the series of fermentation reactors.

3. The method according to claim 1, wherein in the hydrolyzing step (step iii), the sugar hydrolyzate further comprises at least one sugar selected from the group consisting of galactose, xylose, mannose and arabinose.

4. The method according to claim 1, wherein in the fermenting step (step iv), the yeast is capable of converting xylose to ethanol.

5. The method according to claim 1, wherein in the fermenting step (step iv), the yeast is a *Saccharomyces* spp. capable of converting xylose and glucose to ethanol.

6. The method according to claim 1, wherein in the treating step (step vi), the oxidant that is added to the slurry is chlorine dioxide at a concentration of between about 0.5 and about 1500 ppm.

7. The method according to claim 6, wherein in the treating step (step vi), the chlorine dioxide is added to the slurry at a concentration of between about 100 and about 500 ppm.

8. The method according to claim 1, wherein in the treating step (step vi), the concentration of the microbial contaminants in the oxidant-treated slurry is reduced to at least 100-fold lower than that of the yeast.

9. The method according to claim 1, wherein in the treating step (step vi), the concentration of microbial contaminants in the oxidant-treated slurry is reduced below about $10^3$ cfu/mL.

10. The method according to claim 1, wherein in the treating step (step vi), the concentration of yeast cells in the oxidant-treated slurry is from about 10 g/L to about 300 g/L.

11. The method according to claim 10, wherein in the treating step (step vi), the concentration of yeast cells in the oxidant-treated slurry is from about 20 g/L to about 200 g/L.

12. The method according to claim 1, wherein in the treating step (step vi), the temperature of the oxidant-treated slurry is between about 4° C. and about 37° C.

13. The method according to claim 1, wherein in the treating step (step vi), the pH of the oxidant-treated slurry is between about 3 and about 6.

14. The method according to claim 1, wherein in the treating step (step vi), the slurry is contacted with the oxidant for a minimum of about 1 minute to produce said oxidant-treated slurry.

15. The method according to claim 14, wherein in the step of treating step (step vi), the slurry is contacted with the oxidant for a minimum of about 15 minutes to produce said oxidant-treated slurry.

16. The method according to claim 1, wherein the slurry comprising yeast of step (v) is the fermentation broth.

* * * * *